(12) United States Patent
Fiene et al.

(10) Patent No.: US 8,044,166 B2
(45) Date of Patent: Oct. 25, 2011

(54) PROCESS FOR PREPARING PENTAMETHYLENE 1,5-DIISOCYANATE

(75) Inventors: Martin Fiene, Niederkirchen (DE); Eckhard Stroefer, Mannheim (DE); Wolfgang Siegel, Limburgerhof (DE); Stephan Freyer, Neustadt (DE); Oskar Zelder, Speyer (DE); Gerhard Schulz, Bad Duerkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 336 days.

(21) Appl. No.: 12/373,088

(22) PCT Filed: Jul. 25, 2007

(86) PCT No.: PCT/EP2007/057646
§ 371 (c)(1),
(2), (4) Date: Jan. 9, 2009

(87) PCT Pub. No.: WO2008/015134
PCT Pub. Date: Feb. 7, 2008

(65) Prior Publication Data
US 2009/0292100 A1    Nov. 26, 2009

(30) Foreign Application Priority Data
Aug. 1, 2006    (EP) .................................... 06118256

(51) Int. Cl.
*C08G 18/00*    (2006.01)
*C07C 263/12*    (2006.01)
*C07C 263/10*    (2006.01)
*C12P 13/00*    (2006.01)

(52) U.S. Cl. .......... 528/85; 560/348; 560/347; 560/355; 435/128

(58) Field of Classification Search ........................ None
See application file for complete search history.

(56) References Cited

U.S. PATENT DOCUMENTS

| 5,103,045 A * | 4/1992 | Robin et al. ................. 560/335 |
| 2005/0003497 A1* | 1/2005 | Nishi et al. .................... 435/128 |

FOREIGN PATENT DOCUMENTS

| DE | 1 900 514 | | 8/1970 |
| DE | 26 25 075 A1 | | 12/1977 |
| DE | 2625075 | * | 12/1977 |
| EP | 0 259 233 A2 | | 3/1988 |
| EP | 0 161 419 B1 | | 8/1989 |
| EP | 1 482 055 A1 | | 12/2004 |
| GB | 1 225 450 | | 3/1971 |
| WO | WO 03/099768 A1 | | 12/2003 |
| WO | WO 2006/005603 A1 | | 1/2006 |

OTHER PUBLICATIONS

Database Caplus Chemical Abstracts Service, Columbus, Ohio, US 1979, T. Lesiak et al "Preparation of Aliphatic diisocyanates without using phosgene" XP002456997.*
Enzyme Handbook, Dec 1, 1982, by Asakura Shoten.*
Preparation of Aliphatic Diisocyanates without using Phosgene, Jun. 1969, by Sea Lesiak.*
T. Lesiak, et al., "Preparation of aliphatic diisocyanates without using phosgene", Journal f. prakt. Chemie., Band 321, XP002456997, 1979, pp. 161-163, Derwent Abstract attached.
Guy Gautret De La Moricière, et al., "La décarboxylation de la lysine", Bulletin De La Société Chimique De France, No. 12, 1969, pp. 4421-4425.
U.S. Appl. No. 12/446,460, filed Apr. 21, 2009, Boehling et al.

* cited by examiner

*Primary Examiner* — Randy Gulakowski
*Assistant Examiner* — Jeffrey Washville
(74) *Attorney, Agent, or Firm* — Oblon, Spivak, McClelland, Maier & Neustadt, L.L.P.

(57) ABSTRACT

The present invention relates to a process for preparing pentamethylene 1,5-diisocyanate, to pentamethylene 1,5-diisocyanate prepared in this way and to the use thereof.

13 Claims, No Drawings

PROCESS FOR PREPARING PENTAMETHYLENE 1,5-DIISOCYANATE

The present invention relates to a process for preparing pentamethylene 1,5-diisocyanate, to pentamethylene 1,5-diisocyanate prepared in this way and to the use thereof.

The preparation of pentamethylene diisocyanate from 1,5-pentanediamine is known per se and can be effected without phosgene (T. Lesiak, K. Seyda, Journal für Praktische Chemie (Leipzig), 1979, 321(1), 161-163) or by reaction with phosgene (e.g. DE 2625075).

DE 1900514 (corresponding to GB 1225450) describes the two-stage preparation of pentamethylene 1,5-diisocyanate from caprolactam by conversion to the hydroxamic acids and the subsequent phosgenation thereof.

The yield reported in this document for the conversion of caprolactam to pentamethylene 1,5-diisocyanate is only approx. 32%.

Caprolactam is prepared on the industrial scale either in several stages from benzene by ring hydrogenation to cyclohexane, oxidation to cyclohexanone and Beckmann rearrangement with hydroxylamine, or from 1,4-butadiene by hydrocyanation and selective hydrogenation and subsequent cyclization to the caprolactam. In both cases, the basis is a hydrocarbon from petrochemistry.

This is therefore a petrochemistry-based preparation over five stages in each case, proceeding from benzene or from butadiene.

The preparation of 1,5-pentanediamine is known by enzymatic decarboxylation of lysine with, for example, lysine decarboxylase (EP 1482055 A1 or JP 2004-222569 A) in a cell-free system or by thermal or catalytic decarboxylation (G. Gautret de la Moriciere, G. Chatelus, Bull. Soc. Chim. France, 1969, 12, 4421-4425) or by hydrogenation of the corresponding nitriles (for example EP 161419 or WO 2003/99768).

1,5-Pentanediamine has to date not been available on the industrial scale.

WO 2006/005603 describes a biochemical process for preparing 1,4-butanediamine from ornithine with the aid of ornithine decarboxylase and the use thereof as a starting compound for polyamide preparation.

It was an object of the present invention to prepare pentamethylene 1,5-diisocyanate which can be prepared from renewable raw materials.

This object is achieved by a process for preparing pentamethylene 1,5-diisocyanate, in which
b) lysine is converted to 1,5-pentanediamine and
c) the 1,5-pentanediamine thus obtained is converted to pentamethylene 1,5-diisocyanate.

The advantage of the process according to the invention is based on independence from mineral oil as the raw material basis in the preparation of the pentamethylene 1,5-diisocyanate. In addition, the pentamethylene 1,5-diisocyanate prepared in this way has less color than that prepared conventionally, since it is subjected to less thermal stress.

As a result of the inventive selection of the raw material basis of lysine or renewable raw materials, the process according to the invention affords at least virtually isomerically pure pentamethylene 1,5-diisocyanate, whereas the pentamethylene 1,5-diisocyanate prepared by the conventional route comprises a proportion of isomeric pentamethylene diisocyanates, especially pentamethylene 1,4-diisocyanate. Depending on its preparation, this proportion may be up to several % by weight.

The pentamethylene 1,5-diisocyanate prepared in accordance with the invention has, in contrast, a proportion of the branched pentamethylene diisocyanate isomers of in each case less than 100 ppm.

The present process therefore further provides a mixture consisting of at least two different pentamethylene diisocyanate isomers, of which the main constituent is pentamethylene 1,5-diisocyanate, and the isomer present in smaller amounts is present in amounts of not more than 100 ppm, with the proviso that the sum is 100% by weight.

The present process further provides a mixture consisting of pentamethylene 1,5-diisocyanate and pentamethylene 1,4-diisocyanate, where the proportion of pentamethylene 1,4-diisocyanate amounts to not more than 10 000 ppm, preferably 7500 ppm, more preferably 5000 ppm, even more preferably 2500 ppm, in particular 1000 ppm, especially 500 ppm and even 100 ppm, and the proportion of pentamethylene 1,5-diisocyanate makes up the remainder to 100% by weight.

Consequently, the pentamethylene 1,5-diisocyanate prepared in accordance with the invention has virtually exclusively two primary isocyanate groups and therefore exhibits a more homogeneous reactivity in conversions of the isocyanate groups, for example in the preparation of polyurethanes. Branched pentamethylene diisocyanate isomers, in contrast, have one primary and one secondary isocyanate group, which are of different reactivity.

The pentamethylene 1,5-diisocyanate obtained by the process according to the invention generally has a color number of not more than 15 APHA to DIN ISO 6271.

The inventive step b) consists of a conversion of lysine to 1,5-pentanediamine.

Lysine can be used in pure form or can actually be formed in the course of the reaction (see below for step a)). In addition, lysine can in the form of an aqueous solution, buffer solution or in the form of a lysine-containing reaction mixture with a lysine content of preferably from at least 5% by weight up to the solubility limit in the particular reaction mixture at the particular temperatures. In general, the content may be up to 45% by weight, preferably up to 40, more preferably up to 35 and most preferably up to 30% by weight.

The lysine (2,6-diaminohexanoic acid) used for the process according to the invention originates from preferably biological material and may be present in the form of the D enantiomer, in the form of the L enantiomer or in the form of any mixture of these enantiomers, for example in the form of a racemate, preferably in the form of the L enantiomer [(S)-2,6-diaminohexanoic acid].

It can be used in free form or as an internal salt, in the form of its anion as a carboxylate, or mono- or diprotonated in the form of its mono- or diammonium salt, for example as the chloride.

In addition, the lysine can be used in the form of its ester, for example as the methyl, ethyl, n-propyl, isopropyl, n-butyl, sec-butyl or isobutyl ester.

Step b) is preferably a decarboxylation.

In one possible decarboxylation, lysine, if appropriate dissolved or suspended in a solvent, is heated at a temperature above 80° C., preferably above 100° C., more preferably above 120° C., even more preferably above 150° C. and in particular above 180° C. (thermal decarboxylation).

The temperature may be up to 250° C., preferably up to 230° C., more preferably up to 210° C. and most preferably up to 200° C.

If appropriate, pressure can be applied in order to keep any solvent present in the reaction mixture.

Examples of solvents are aromatic and/or (cyclo)aliphatic hydrocarbons and mixtures thereof, halogenated hydrocarbons, esters, ethers and alcohols.

Preference is given to aromatic hydrocarbons, (cyclo)aliphatic hydrocarbons, alkyl alkanoates, alkoxylated alkyl alkanoates and mixtures thereof.

Particular preference is given to mono- or polyalkylated benzenes and naphthalenes, alkyl alkanoates and alkoxylated alkyl alkanoates, and mixtures thereof.

Preferred aromatic hydrocarbon mixtures are those which comprise predominantly aromatic $C_7$- to $C_{1-4}$-hydrocarbons and may comprise a boiling range of from 110 to 300° C.; particular preference is given to toluene, o-, m- or p-xylene, trimethylbenzene isomers, tetramethylbenzene isomers, ethylbenzene, cumene, tetrahydronaphthalene and mixtures comprising them.

Examples thereof are the Solvesso® brands from Exxon-Mobil Chemical, particularly Solvesso® 100 (CAS No. 64742-95-6, predominantly $C_9$ and $C_{10}$ aromatics, boiling range about 154-178° C.), 150 (boiling range about 182-207° C.) and 200 (CAS No. 64742-94-5), and the Shellsol® brands from Shell. Hydrocarbon mixtures composed of paraffins, cycloparaffins and aromatics are also commercially available under the names Kristalloel (for example Kristalloel 30, boiling range about 158-198° C. or Kristalloel 60: CAS No. 64742-82-1), white spirit (for example likewise CAS No. 64742-82-1) or solvent naphtha (light: boiling range about 155-180° C., heavy: boiling range about 225-300° C.). The aromatics content of such hydrocarbon mixtures is generally more than 90% by weight, preferably more than 95, more preferably more than 98 and most preferably more than 99% by weight. It may be advisable to use hydrocarbon mixtures with a particularly reduced content of naphthalene.

Halogenated hydrocarbons are, for example, chlorobenzene and dichlorobenzene or isomer mixtures thereof.

Esters are, for example, n-butyl acetate, ethyl acetate, 1-methoxy-2-propyl acetate and 2-methoxyethyl acetate, and the mono- and diacetyl esters of ethylene glycol, diethylene glycol, triethylene glycol, propylene glycol, dipropylene glycol or tripropylene glycol, for example butylglycol acetate. Further examples are also carbonates, such as preferably 1,2-ethylene carbonate, 1,2-propylene carbonate or 1,3-propylene carbonate.

Ethers are, for example, tetrahydrofuran (THF), dioxane and the dimethyl, ethyl or n-butyl ethers of ethylene glycol, diethylene glycol, triethylene glycol, propylene glycol, dipropylene glycol or tripropylene glycol.

(Cyclo)aliphatic hydrocarbons are, for example, decalin, alkylated decalin and isomer mixtures of linear or branched alkanes and/or cycloalkanes.

Alcohols are, for example, methanol, ethanol, n-propanol, isopropanol, n-butanol, sec-butanol, isobutanol, pentanol isomer mixtures, hexanol isomer mixtures, 2-ethylhexanol or octanol.

Water is particularly suitable.

For the decarboxylation, it is additionally also possible to add a base, for example an organic base, preferably an amine, more preferably a secondary or tertiary amine, or an inorganic base, for example alkali metal or alkaline earth metal oxides, hydroxides, carbonates or hydrogencarbonates, preferably sodium hydroxide solution, potassium hydroxide solution, sodium hydrogencarbonate, sodium carbonate, potassium hydrogencarbonate, calcium hydroxide, milk of lime or potassium carbonate (catalytic decarboxylation).

Especially when lysine is used in the form of an ester, preferably of the methyl ester, performance of the reaction as a dealkoxycarbonylation under so-called "Krapcho" conditions is preferred, in which case a nucleophile, preferably an iodide or bromide, more preferably an iodide, is added to the reaction mixture which is heated under these reaction conditions.

However, particular preference is given to performing the decarboxylation with the aid of an enzyme.

The enzymes are preferably lyases (E.C. 4.-.-.-), more preferably carbon-carbon lyases (E.C. 4.1.-.-) and most preferably carboxy lyases (E.C. 4.1.1.-)

Examples Thereof are:
EC 4.1.1.1 pyruvate decarboxylase
EC 4.1.1.2 oxalate decarboxylase
EC 4.1.1.3 oxaloacetate decarboxylase
EC 4.1.1.4 acetoacetate decarboxylase
EC 4.1.1.5 acetolactate decarboxylase
EC 4.1.1.6 aconitate decarboxylase
EC 4.1.1.7 benzoylformate decarboxylase
EC 4.1.1.8 oxalyl-CoA decarboxylase
EC 4.1.1.9 malonyl-CoA decarboxylase
EC 4.1.1.11 aspartate 1-decarboxylase
EC 4.1.1.12 aspartate 4-decarboxylase
EC 4.1.1.14 valine decarboxylase
EC 4.1.1.15 glutamate decarboxylase
EC 4.1.1.16 hydroxyglutamate decarboxylase
EC 4.1.1.17 ornithine decarboxylase
EC 4.1.1.18 lysine decarboxylase
EC 4.1.1.19 arginine decarboxylase
EC 4.1.1.20 diaminopimelate decarboxylase
EC 4.1.1.21 phosphoribosylaminoimidazole carboxylase
EC 4.1.1.21 phosphoribosylaminoimidazole carboxylase
EC 4.1.1.22 histidine decarboxylase
EC 4.1.1.23 orotidine-5'-phosphate decarboxylase
EC 4.1.1.24 aminobenzoate decarboxylase
EC 4.1.1.25 tyrosine decarboxylase
EC 4.1.1.28 aromatic-L-amino-acid decarboxylase
EC 4.1.1.29 sulfoalanine decarboxylase
EC 4.1.1.30 pantothenoylcysteine decarboxylase
EC 4.1.1.31 phosphoenolpyruvate carboxylase
EC 4.1.1.32 phosphoenolpyruvate carboxykinase (GTP)
EC 4.1.1.33 diphosphomevalonate decarboxylase
EC 4.1.1.34 dehydro-L-gulonate decarboxylase
EC 4.1.1.35 UDP-glucuronate decarboxylase
EC 4.1.1.36 phosphopantothenoylcysteine decarboxylase
EC 4.1.1.37 uroporphyrinogen decarboxylase
EC 4.1.1.38 phosphoenolpyruvate carboxykinase (diphosphate)
EC 4.1.1.39 ribulose-bisphosphate carboxylase
EC 4.1.1.40 hydroxypyruvate decarboxylase
EC 4.1.1.41 methylmalonyl-CoA decarboxylase
EC 4.1.1.42 carnitine decarboxylase
EC 4.1.1.43 phenylpyruvate decarboxylase
EC 4.1.1.44 4-carboxymuconolactone decarboxylase
EC 4.1.1.45 aminocarboxymuconate-semialdehyde decarboxylase
EC 4.1.1.46 o-pyrocatechuate decarboxylase
EC 4.1.1.47 tartronate-semialdehyde synthase
EC 4.1.1.48 indole-3-glycerol-phosphate synthase
EC 4.1.1.49 phosphoeno/pyruvate carboxykinase (ATP)
EC 4.1.1.50 adenosylmethionine decarboxylase
EC 4.1.1.51 3-hydroxy-2-methylpyridine-4,5-dicarboxylate 4-decarboxylase
EC 4.1.1.52 6-methylsalicylate decarboxylase
EC 4.1.1.53 phenylalanine decarboxylase
EC 4.1.1.54 dihydroxyfumarate decarboxylase
EC 4.1.1.55 4,5-dihydroxyphthalate decarboxylase
EC 4.1.1.56 3-oxolaurate decarboxylase
EC 4.1.1.57 methionine decarboxylase EC 4.1.1.58 orsellinate decarboxylase
EC 4.1.1.59 gallate decarboxylase
EC 4.1.1.60 stipitatonate decarboxylase
EC 4.1.1.61 4-hydroxybenzoate decarboxylase
EC 4.1.1.62 gentisate decarboxylase
EC 4.1.1.63 protocatechuate decarboxylase
EC 4.1.1.64 2,2-dialkylglycine decarboxylase (pyruvate)
EC 4.1.1.65 phosphatidylserine decarboxylase
EC 4.1.1.66 uracil-5-carboxylate decarboxylase
EC 4.1.1.67 UDP-galacturonate decarboxylase
EC 4.1.1.68 5-oxopent-3-ene-1,2,5-tricarboxylate decarboxylase
EC 4.1.1.69 3,4-dihydroxyphthalate decarboxylase
EC 4.1.1.70 glutaconyl-CoA decarboxylase
EC 4.1.1.71 2-oxoglutarate decarboxylase
EC 4.1.1.72 branched-chain-2-oxoacid decarboxylase
EC 4.1.1.73 tartrate decarboxylase
EC 4.1.1.74 indolepyruvate decarboxylase
EC 4.1.1.75 5-guanidino-2-oxopentanoate decarboxylase
EC 4.1.1.76 arylmalonate decarboxylase
EC 4.1.1.77 4-oxalocrotonate decarboxylase
EC 4.1.1.78 acetylenedicarboxylate decarboxylase
EC 4.1.1.79 sulfopyruvate decarboxylase
EC 4.1.1.80 4-hydroxyphenylpyruvate decarboxylase
EC 4.1.1.81 threonine-phosphate decarboxylase
EC 4.1.1.82 phosphonopyruvate decarboxylase
EC 4.1.1.83 4-hydroxyphenylacetate decarboxylase
EC 4.1.1.84 D-dopachrome decarboxylase
EC 4.1.1.85 3-dehydro-L-gulonate-6-phosphate decarboxylase Especially preferred is the (enzymatic decarboxylation) in the presence of lysine decarboxylase (E.C. 4.1.1.18, particularly CAS No. 9024-76-4).

It is at first not necessary to distinguish between performance of step b) in a cell-free system and a fermentative performance. However, a particularly preferred embodiment of the present invention consists in preparing the 1,5-pentanediamine from suitable substrates fermentatively by means of living microorganisms.

Particular preference is given to performing the decarboxylation in the presence of genetically modified microorganisms, as described, for example, in EP 1482055 and in international patent application PCT/EP2007/052783 filed Mar. 23, 2007, with the title "Process for the production of cadaverine", both of which are hereby incorporated by reference in this disclosure.

Preferred microorganisms are genetically modified recombinant microorganisms which bear genes with lysine decarboxylase activity, preferably the cadA gene (Kyoto Encyclopedia of Genes and Genomes, Entry b4131) and the ldcC gene (Kyoto Encyclopedia of Genes and Genomes, Entry JW0181) of *Escherichia coli.*

The microorganisms are more preferably *Corynebacteria* and more preferably *Corynebacterium glutamicum.*

A particularly preferred embodiment of the present invention is to perform, instead of step b) (conversion of lysine to 1,5-pentanediamine), a one-stage synthesis of 1,5-pentanediamine proceeding from a suitable substrate in a step a). This comprises the step b) generally in the form of an intracellular conversion of the substrate to lysine and then the likewise intracellular conversion of lysine to 1,5-pentanediamine.

It is of no importance in the context of the invention whether lysine is isolated in pure form, is present in a mixture obtained as an intermediate or is formed merely as an intermediate, for example intracellularly, in the course of step a). In the latter variant, it is additionally of no importance whether lysine is actually formed as an intermediate or whether the intermediate merely has a lysine base structure and, for example, the carboxyl group is esterified or the amino groups are substituted.

Without wishing to be bound to a theory, it is suspected that, in the biosynthesis of lysine, a monosaccharide is converted via a number of intermediates to aspartic acid which, after conversion to 4-oxo-2-aminobutyric acid, reacts with pyruvate to give the dihydropicoline-2,6-dicarboxylic acid intermediate. This is converted to tetrahydropicoline-2,6-dicarboxylic acid which finally reacts to give diaminopimelic acid which is converted to lysine by decarboxylation.

A preferred process for performing step a) is described in international patent application PCT/EP2007/052783, filed Mar. 23, 2007, with the title "Process for the production of cadaverine", which is hereby incorporated by reference in this disclosure.

Suitable substrates for the reaction are renewable raw materials. According to the definition of Römpp-Online, under "Nachwachsende Rohstoffe" [Renewable Raw Materials], document RD-14-00046, as available August 2005, they are products obtained in agriculture and forestry which are sent to a use in the nonfood sector. The renewable raw materials accordingly include both primary raw materials, such as wood, and products from the first and second processing stage, such as cellulose, starch, monomeric carbohydrates, chitin, animal or vegetable fats and oils, and proteins and animal products, for example virgin wool, leather and skins, tallow, gelatin and casein, and organic residues, such as straw. Starch may, for example, be that from potatoes, cassava, cereal, for example wheat, maize, barley, rye, triticale or rice, and various millet types, for example sorghum and milo.

Particularly suitable substrates are monosaccharides, oligosaccharides and polysaccharides of pentoses and/or hexoses, for example mannose, galactose, sorbose, xylose, arabinose, ribose, glucose, sucrose, lactose, fructose, maltose, molasses, starch or cellulose, but also oils and fats, for example soybean oil, sunflower oil, groundnut oil, coconut oil or rapeseed oil, or fatty acids, for example palmitic acid, stearic acid and linolenic acid, or alcohols such as glycerol and ethanol, or organic acids, for example acetic acid. In a preferred embodiment, glucose, fructose or sucrose is used as the carbon source. These compounds may be used individually or as a mixture.

A preferred process for converting starch to lysine is, for example, described in WO 05/116228, which is hereby incorporated by reference in this disclosure.

The nitrogen sources used may be organic compounds which comprise nitrogen, for example peptone, yeast extract, meat extract, malt extract, soybean flour and urea, or inorganic compounds such as ammonium sulfate, ammonium chloride, ammonium phosphate, ammonium carbonate and ammonium nitrate, or a mixture of the compounds mentioned.

Phosphorus sources which can be used are phosphoric acid, potassium dihydrogenphosphate, dipotassium hydrogenphosphate, or the corresponding sodium compounds.

The culture medium may further comprise metal salts, for example magnesium sulfate or iron sulfate, which are needed for growth.

In addition, essential growth-promoting compounds, for example amino acids or vitamins, may be used in addition to the abovementioned compounds. Corresponding precursors can likewise be added to the culture medium.

The enzymatic decarboxylation is effected generally at from 0 to 100° C., preferably from 20 to 80° C., more preferably from 20 to 70° C., most preferably from 20 to 60° C.

The pH of the culture medium is generally kept between 6.0 and 8.5.

The enzyme content in the reaction medium is generally in the range from about 0.1 to 10% by weight, based on the lysine used.

The reaction time depends upon factors including the temperature, the amount used and the activity of the enzyme catalyst or of the microorganism, and on the required conversion. Preference is given to adjusting the reaction time such that the conversion of all carboxyl functions originally present in the lysine is at least 70%, preferably at least 80, more preferably at least 90, even more preferably at least 95%, in particular at least 98% and especially at least 99%. In general, from 1 to 48 hours and preferably from 1 to 12 hours are sufficient for this purpose.

It may be necessary to pass oxygen through the reaction mixture.

The reaction can proceed in organic solvents or mixtures thereof or without addition of solvents. However, the solvent used may also be water.

The proportion of organic solvents is, for example, 0.01-90% by weight. Suitable organic solvents are those known for these purposes, for example tertiary monools such as $C_3$-$C_6$-alcohols, preferably tert-butanol, tert-amyl alcohol, pyridine, poly-$C_1$-$C_4$-alkylene glycol di-$C_1$-$C_4$-alkyl ethers, preferably polyethylene glycol di-$C_1$-$C_4$-alkyl ethers, for example 1,2-dimethoxyethane, diethylene glycol dimethyl ether, polyethylene glycol dimethyl ether 500, $C_1$-$C_4$-alkylene carbonates, especially propylene carbonate, $C_3$-$C_6$-alkyl acetates, especially tert-butyl acetate, THF, toluene, 1,3-dioxolane, acetone, isobutyl methyl ketone, ethyl methyl ketone, 1,4-dioxane, tert-butyl methyl ether, cyclohexane, methylcyclohexane, toluene, hexane, dimethoxymethane, 1,1-dimethoxyethane, acetonitrile, and the mono- or polyphasic mixtures thereof.

Optionally, aqueous solvents can be added to the organic solvents, so as to give rise to mono- or polyphasic reaction solutions according to the organic solvent. Examples of aqueous solvents are water and aqueous, dilute (e.g. 10 to 100 mM) buffers, for example having a pH in the range from about 6 to 8, for example potassium phosphate or Tris-HCl buffers.

The substrates are present in the reaction medium in dissolved form, suspended as solids or in emulsion. The initial concentration of the reactants is preferably in the range from about 0.1 to 20 mol/l, especially from 0.15 to 10 mol/l or from 0.2 to 5 mol/l.

The reaction can be effected continuously, for example in a tubular reactor or in a stirred reactor battery, or batchwise.

The reaction can be carried out in all reactors suitable for such a reaction. Such reactors are known to those skilled in the art. Preference is given to effecting the reaction in a stirred tank reactor or a fixed bed reactor.

To mix the reaction mixture, any desired methods can be used. Specific stirred apparatus is not required. The reaction medium may be mono- or polyphasic and the reactants are dissolved, suspended or emulsified therein, if appropriate initially charged and admixed with the enzyme preparation at the start of the reaction, and if appropriate once or more than once in the course of the reaction. The temperature is set to the desired value during the reaction and can, if desired, be increased or reduced during the course of the reaction.

When the reaction is performed in a fixed bed reactor, the fixed bed reactor is preferably equipped with immobilized enzymes, in which case the reaction mixture is pumped through a column filled with the enzyme. It is also possible to perform the reaction in a fluidized bed, in which case the enzyme is used immobilized on a carrier. The reaction mixture can be pumped continuously through the column, in which case the flow rate can be used to control the residence time and hence the desired conversion. It is also possible to pump the reaction mixture through a column in circulation.

After the reaction has ended, the reaction mixture obtainable from b) or a) can be used further without further purification, or it can preferably be purified before it is used in step c).

In general, the reaction mixture obtained from the preceding reaction step comprises, as well as 1,5-pentanediamine and water, also unconverted substrate, metabolites of the substrate used and if appropriate organic solvents, and additionally possibly enzyme, intact or lyzed microorganisms.

In general, only the enzyme used is removed and from the reaction mixture, and the reaction product is removed from any organic solvent used.

Enzyme is removed generally by crystallization, precipitation, chromatography, reverse osmosis, electrophoresis, electrodialysis, extraction, distillation, filtration, absorption, centrifugation or decantation. The enzyme removed can subsequently be used for further reactions.

A removal of microorganisms or lysate is effected generally by extraction, distillation, filtration, absorption, batchwise or continuous centrifugation, crossflow centrifugation or decantation. Intact microorganisms removed can subsequently be used for further reactions.

Before the removal, microorganisms, if desired, can also be disrupted, for example by shearing.

The removal from the organic solvent is effected generally by distillation, rectification.

For the distillation, a distillation column having from 1 to 20 theoretical plates can be attached to the reaction vessel, in which the reflux can be adjusted to the separation requirements. In the case of low-boiling organic solvents, can also a one-stage distillation by means of flash, falling-film, thin-film, short-path and/or wiper-blade evaporators, to which a short column may be attached if appropriate.

The removal of the low boilers from the reaction mixture can be supported by passing through a gas stream which is essentially inert under the reaction conditions (stripping), for example an oxygen-depleted mixture of air and nitrogen (lean air), or preferably nitrogen or carbon dioxide.

The water is then removed preferably continuously or stepwise in a manner known per se, for example by means of reduced pressure, azeotropic removal, absorption, pervaporation and diffusion through membranes.

It may also be possible to convert 1,5-pentanediamine to a salt, preferably to the hydrochloride, and to precipitate it with water-soluble organic solvents, for example alcohols or acetone. In this case, the precipitate can be purified by washing and/or crystallization, and the 1,5-diamine can subsequently be released again by adding a base.

For the absorption, molecular sieves or zeolites (pore size, for example, in the range of about 3-1 0 angstrom) are preferably suitable, or alternatively a removal by distillation or with the aid of suitable semipermeable membranes.

The 1,5-pentanediamine thus obtained can, if required, be distilled once more, such that the purity is generally at least 98%, preferably at least 99%, more preferably at least 99.5% and most preferably at least 99.8%.

Step c) can be effected without phosgene or in the presence of phosgene; in the latter variant, the phosgenation can be effected in the liquid phase or in the gas phase.

Phosgene-free processes for preparing isocyanates are known, for example, from EP 18588 A1, EP 28338 A2, EP 27952, EP 126299 and particularly EP 566925 A2.

The phosgene-free processes known in the prior art can be employed for the process according to the invention, but preferably the process described below:

To prepare the urethanes, the amine is reacted with urea and at least one, preferably exactly one, alcohol in a molar ratio of amine, urea and alcohol such as 1:2 to 20:5 to 40 at temperatures of 50-300° C. and especially at 180-220° C., under a pressure of from 0.1 to 30 bar, preferably 5-20 bar. These reaction conditions result in mean reaction times of fractions of seconds to minutes for the process.

The reaction can be performed in the presence of dialkyl carbonates, appropriately in an amount of from 0.1 to 30 mol %, preferably from 1 to 10 mol %, or alkyl carbamates, appropriately in an amount of from 1 to 20 mol %, preferably from 5 to 15 mol %, based on the diamine. In particular, mixtures of dialkyl carbonates and alkyl carbamates are used in the quantitative ratios specified. The dialkyl carbonates and/or carbamic esters used are preferably those whose alkyl radicals correspond to the alkyl radical of the alcohol used.

The reaction can also be effected in the presence of catalysts. These are appropriately used in amounts of from 0.001 to 20% by weight, preferably from 0.001 to 5% by weight, especially from 0.01 to 0.1% by weight, based on the weight of the amine.

Suitable catalysts are inorganic or organic compounds which comprise one or more cations, preferably a cation of metals of group IA, IB, IIA, IIB, IIIB, IVA, IVB, VA, VB, VIIB, VIIB, VIIIB of the periodic table of the elements, defined according to Handbook of Chemistry and Physics 14th Edition, published by Chemical Rubber Publishing Co., 23 Superior Ave. N.E., Cleveland, Ohio. Examples include the cations of the following metals: lithium, sodium, potassium, magnesium, calcium, aluminum, gallium, tin, lead, bismuth, antimony, copper, silver, gold, zinc, mercury, cerium, titanium, vanadium, chromium, molybdenum, manganese, iron and cobalt.

The catalyst may further comprise at least one anion, for example halides such as chlorides and bromides, sulfates, phosphates, nitrates, borates, alkoxides, phenoxides, sulfonates, oxides, oxide hydrates, hydroxides, carboxylates, chelates, carbonates and thio- or dithiocarbamates.

The catalysts can also be used in the form of their hydrates or ammoniates without any perceptible significant disadvantages.

Examples of typical catalysts include the following compounds: lithium methoxide, lithium ethoxide, lithium propoxide, lithium butoxide, sodium methoxide, potassium tert-butoxide, magnesium methoxide, calcium methoxide, tin(II) chloride, tin(IV) chloride, lead acetate, lead phosphate, antimony(III) chloride, antimony(V) chloride, aluminum acetylacetonate, aluminum isobutoxide, aluminum trichloride, bismuth(III) chloride, copper(II) acetate, copper(II) sulfate, copper(II) nitrate, bis(triphenylphosphinoxido)-copper(II) chloride, copper molybdate, silver acetate, gold acetate, zinc oxide, zinc chloride, zinc acetate, zinc acetonylacetate, zinc octoate, zinc oxalate, zinc hexoxide, zinc benzoate, zinc undecylenoxide, cerium(IV) oxide, uranyl acetate, titanium tetrabutoxide, titanium tetrachloride, titanium tetraphenoxide, titanium naphthenate, vanadium(III) chloride, vanadium acetylacetonate, chromium(III) chloride, molybdenum(VI) oxide, molybdenum acetylacetonate, tungsten(VI) oxide, manganese(II) chloride, manganese(II) acetate, manganese(III) acetate, iron(II) acetate, iron(III) acetate, iron phosphate, iron oxalate, iron(III) chloride, iron(III) bromide, cobalt acetate, cobalt chloride, cobalt sulfate, cobalt naphthenate, nickel chloride, nickel acetate and nickel naphthenate, and mixtures thereof.

Examples of preferred catalysts include the following compounds: lithium butoxide, aluminum acetylacetonate, zinc acetylacetonate, titanium tetrabutoxide and zirconium tetrabutoxide.

The reactant streams can preferably be mixed in a suitable specific mixing unit which is notable for low mixing times.

The mixed reactant stream is then conducted into a reaction unit which can be configured with backmixing or as a tubular reactor or as a combination thereof.

The reaction mixture is converted in the reactor at a mean of from 10 seconds to 5 hours, preferably from 20 seconds to 20 minutes, more preferably from 30 seconds to 10 minutes. The temperature is generally between 50° C. and 300° C., preferably between 180° C. and 220° C. The pressure is generally between 0.1 bar abs and 30 bar abs and preferably between 5 and 20 bar abs.

The residence time is selected such that the conversion, based on amino groups in the amine used to urethane groups, after leaving the reactor, is at least 95%, preferably at least 98, more preferably at least 99 and most preferably at least 99.5%.

When the conversion, based on amino groups in the amine used to urethane groups, after leaving the reactor, is still incomplete and is, for example, less than 95%, the discharge can be reacted further once again.

To remove the ammonia, columns are appropriately used; preference is given to removing the ammonia by distillation. This achieves a good separation between the alcohol and ammonia. Typically, the removal is effected within a pressure range of 0.01-20 bar, preferably at 0.04-15 bar. The temperatures necessary are guided by the alcohol used or the alcohol mixture. For n-butanol the temperature is, for example, 60-150° C., preferably from 80 to 140° C.

It has been found to be advantageous to remove the ammonia formed from the reaction mixture immediately, such that coverage by ammonium carbamate, which is formed in minimal amounts from ammonia and carbon dioxide as a result of decomposition of urea, can be prevented.

This distillation unit is of a design known per se and has the customary internals. Useful column internals include in principle all common internals, for example trays, structured packings and/or random packings. Among the trays, preference is given to bubble-cap trays, sieve trays, valve trays, Thormann trays and/or dual-flow trays; among the random packings, preference is given to those comprising rings, helices, saddles, Raschig, Intos or Pall rings, barrel or Intalox saddles, Top-Pak, etc., or braids. Preference is given to using trays, particular preference to bubble-cap trays.

The distillation column has preferably 10-20 theoretical plates.

Alcohol, dialkyl carbonates, if they are formed or are present in the reaction mixture, or alkyl carbamates or mixtures of at least two of these components are then removed from the resulting ammonia-depleted reaction mixture and preferably recycled into the reaction stage.

To remove the components, the reaction mixture is advantageously decompressed from the pressure level of the reaction stage to a pressure in the range from 1 to 500 mbar, preferably from 10 to 100 mbar. This affords gaseous vapors which comprise the predominant amount of alcohol and from 0 to 30% by weight, preferably from 1 to 10% by weight, of dialkyl carbonate and/or from 1 to 50% by weight, preferably from 1 to 20% by weight, of alkyl carbamate, and a liquid discharge which consists essentially of the monomeric diurethane, with or without oligourea polyurethanes and high-boiling oligomers.

The resulting vapors are separated in downstream, appropriately distillative purification stages, preferably by rectification, and the alcohol and alkyl carbamate products of value isolated here, individually or as a mixture, are preferably recycled into the reaction stage to form the monomeric urethanes.

For the distillative removal of the alcohol or of the alcohol mixture, a so-called flash is frequently used. This apparatus may be a vessel or a combination of a vessel and a column, preferably a column, and it is possible to draw off the alcohol or the alcohol mixture in the tops and the urethane in the bottoms. The tops of the column may, as well as the alcohol, also comprise further substances having a lower boiling point than the urethane. The separation is effected in a pressure range of from 0.001 to 1 bar, preferably at 0.02-0.5 bar.

The liquid reaction mixture which is generally obtained as the bottom discharge after removal of the vapors and comprising the monomer diurethanes, with or without oligourea polyurethanes and high-boiling oligomers, can either be conducted fully into the next stage or is preferably divided into two substreams, in which case the weight ratio of the portions is 5 to 50:95 to 50 parts by weight, preferably 10 to 30:90 to 70 parts by weight.

The portion which is of equal size or preferably smaller is separated by distillation by means of a customary distillation system, preferably of a thin-film evaporator, at a temperature of from 170 to 240° C., preferably from 180 to 230° C., and under a pressure of from 0.001-1 bar, preferably 0.002-0.01 bar, into a product of value which comprises the diurethanes and the lower-boiling by-products, and undistillable by-products which are removed from the preparation process and typically discarded as an unutilizable residue. The product of value (distillate) is combined with the other portion which is of equal size or preferably larger, and the combined reaction mixture comprising diurethanes is sent to the thermal cleavage.

This process measure limits the proportion of undistillable by-products in the reaction mixture, which form in the successive part-reactions and would be constantly enriched as a result of the recycling of utilizable feedstock in the reaction cycle, to a content of from 3 to 30% by weight, preferably from 5 to 20% by weight, as a result ensuring a reaction which proceeds without disruption and with high selectivity.

The distillation units used may be thin-film evaporators or short-path evaporators. The urethane is distilled at pressures of 0.001-1 bar, preferably in the range of 0.002-0.01 bar. The distillate is sent to the cleavage.

The bottoms comprising high boilers are preferably discarded or can, less preferably, partly be fed back to the reurethanization.

The diurethane-comprising reaction mixture thus obtained is cleaved thermally and continuously in a suitable apparatus, preferably without solvent, in the liquid phase in the presence of catalysts at temperatures of from 200 to 300° C., preferably from 220 to 280° C., and under a reduced pressure of 0.01-0.6 bar, preferably in the range of 0.02-0.1 bar. The conversion of diurethane to diisocyanate in the apparatus for thermal cleavage can be selected substantially freely and is appropriately within a range of from 10 to 98% by weight, preferably from 40 to 90% by weight, of the amount supplied.

The uncleaved proportion of the reaction mixture, which comprises unconverted diurethanes, oligourea polyurethanes, high-boiling oligomers and other reutilizable and unutilizable by-products, is removed, discharged continuously from the cleavage apparatus and recycled into the reaction stage directly or if appropriate after reaction with alcohol in the reurethanization.

The catalysts used for chemical cleavage are, for example, the aforementioned inorganic and organic compounds which catalyze urethane formation.

Particularly useful catalysts, which are therefore used with preference, have been found to be dibutyltin dilaurate, iron (III) acetylacetonate, cobalt(II) acetylacetonate, zinc acetylacetonate, zirconium tetra-n-butoxide and tin(II) dioctoate.

Suitable cleavage apparatus is, for example, cylindrical cleavage reactors, for example tubular ovens, or preferably evaporators, for example thin-film or bulk evaporators, for example Robert evaporators, Herbert evaporators, caddle-type evaporators, plate-type cleavers and preferably heating cartridge evaporators.

The cleavage products are separated in a column in which, typically, the isocyanate is drawn off at the side and the alcohol at the top.

The crude isocyanate mixture is freed in a subsequent distillation of recombination products, by-products and, if present, the solvent. The by-products are preferably recycled into the thermal cleavage. A portion can also be discharged.

The cleavage products formed in the thermal cleavage, which are composed in particular of alcohol, diisocyanate and partially cleaved diurethanes, are then advantageously separated with the aid of one or more distillation columns, preferably by rectification at temperatures of from 100 to 220° C., preferably from 120 to 170° C., and a pressure of from 1 to 200 mbar, preferably from 5 to 50 mbar, into low boilers and particularly alcohol, and a crude diisocyanate mixture having a diisocyanate content of from 85 to 99% by weight, preferably from 95 to 99% by weight. The higher-boiling by-products obtained in the distillative separation and especially the uncleaved and partially cleaved diurethanes are preferably conducted into the cleavage apparatus and/or reurethanization.

The crude isocyanate mixture obtained, preferably by rectification, is purified by distillation at a temperature of from 100 to 180° C. and under a pressure of from 1 to 50 mbar, the individual fractions being recycled or isolated as a pure product. As has already been stated, in the purifying distillation preferably employed, the top fraction which preferably consists of diisocyanate, if appropriate after reaction of the free isocyanate groups with alcohol, is recycled into the reaction stage, the side fraction which consists of pure diisocyanate, preferably with a purity of at least 98% by weight, especially more than 99% by weight, is discharged and sent to storage, and the bottom fraction, which comprises the partially cleaved diurethanes and diisocyanates as essential components, is preferably recycled into the cleavage apparatus for thermal cleavage.

The conversion of the reaction discharge and/or distillation residues are preferably fed back to the process. There, alcohol is used to convert the isocyanate groups and/or allophanates and/or ureas and/or other reactive constituents present in this mixture to urethanes. There is the possibility of performing these reactions in separate reactors, for example mixing reactors or flow tubes, or else in. For the alcoholysis of the residues, temperatures of 100-250° C., preferably 150-220° C., are required. The mean residence times are in the range from a few minutes to hours.

To this end, it is possible, for example, to combine the streams with alcohol, in which case the molar ratio of NCO groups or equivalents thereof, i.e., for example, urethane groups, to hydroxyl groups is up to 1:100, preferably up to 1:20, more preferably up to 1:10.

This reaction mixture is converted in the presence or absence of catalysts within from 1 to 150 min, preferably from 3 to 60 min, at a temperature of from 20 to 200° C., preferably from 50 to 170° C., at a pressure of from 0.5 to 20 bar, preferably from 1 to 15 bar.

The reaction can be carried out in a continuous tank battery or in a tubular reactor.

Useful catalysts include in principle all compounds which promote the reaction of NCO groups with OH groups. Examples include tin octoate, dibutyltin dilaurate, tin chloride, zinc dichloride, tin(II) dioctoate and triethylamine.

The performance of the phosgenation in the liquid phase is likewise known per se and can preferably be performed as follows:

The 1,5-pentanediamine obtained from step b) is, if appropriate, predissolved in a solvent either in free form or as the hydrochloride.

The water content of the 1,5-pentanediamine used in stage c) is guided by the type of reaction in stage c) and should, in the case of a phosgenation, preferably be below 200 ppm by weight, and in the case of a phosgene-free procedure preferably below 10% by weight, more preferably below 1% by weight and most preferably below 1000 ppm by weight.

Preference is given to chlorobenzene, o- or p-dichlorobenzene, trichlorobenzene, chlorotoluenes, chloroxylenes, chloroethylbenzene, chloronaphthalenes, chlorodiphenyls, methylene chloride, perchloroethylene, toluene, xylenes, hexane, decahydronaphthalene, diethyl isophthalate (DEIP) and other carboxylic esters as listed, for example, in U.S. Pat. No. 5,136,086, column 3 lines 3 to 18, tetrahydrofuran (THF), dimethylformamide (DMF), benzene and mixtures thereof. Particular preference is given to chlorobenzene and dichlorobenzene.

The content of amine in the amine/solvent mixture is typically between 1 and 50% by mass, preferably between 2 and 40% by mass, more preferably between 3 and 30% by mass.

The phosgene is used as a mixture with the same solvent or another inert solvent, preferably the same solvent, or in pure form. The phosgene used is more preferably at least partly a recycled stream from the workup which has been supplemented with fresh phosgene according to the desired stoichiometry.

The phosgene can be used in the process according to the invention generally in the form of from 10 to 100% by weight, preferably from 30 to 95% by weight and especially from 40 to 90% by weight solutions in inert solvents, preference being given to using the same solvent for the phosgene as for the amine.

The temperature of the phosgene solution should be between −35° C. and 180° C., preferably between −30° C. and 150° C.

For example, the temperature of the amine feed to the mixing unit may be between 10 and 150° C., preferably 15-120° C. and more preferably 20-100° C.

The molar ratio of total phosgene fed into the reaction to amino groups used is generally from 1.1:1 to 30:1, preferably from 1.3:1 to 25:1.

The reactant streams are mixed preferably in a suitable specific mixing unit which is notable for low mixing times.

The mean residence time in the reaction after the mixing is generally from 5 min to 15 h, preferably from 10 min to 12 h, more preferably from 15 min to 10 h.

The temperature in the reaction is generally between 90° C. and 250° C., preferably between 100° C. and 240° C. and more preferably between 110 and 230° C.

The pressure in the reaction is generally between 1.1 bar and 80 bar abs, preferably between 1.5 and 50 bar abs, more preferably between 2 and 35 bar abs, even more preferably between 3 and 10 bar abs, and especially between 4 and 8 bar abs.

The reaction can be effected in a back mixed reactor or in a tubular reactor, or else in a combination of a back mixed reactor to which a tubular reactor is connected downstream.

The reaction mixture is subsequently purified by distillation.

For example, the apparatus may be a distillation column. This distillation unit is of a design known per se and has the customary internals. Useful column internals include in principle all common internals, for example trays, structured packings and/or random packings. Among the trays, preference is given to bubble-cap trays, sieve trays, valve trays, Thormann trays and/or dual-flow trays; among the random packings, preference is given to those comprising rings, helices, saddles, Raschig, Intos or Pall rings, barrel or Intalox saddles, Top-Pak, etc., or braids. Preference is given to using trays, particular preference to bubble-cap trays.

This distillation column has preferably 10-80 theoretical plates.

In this column, the gas phase is conducted through the column from the bottom upward and the liquid phase from the top downward.

The gas phase is generated in the bottom of the column through the operation of an evaporator which may be incorporated into the bottom, for example a Robert evaporator, or in circulation with an external evaporator, for example tube or plate heat exchanger.

A circulation is then, for example, a forced circulation or a natural circulation. Preference is given to evaporating in a natural circulation.

A further inventive consists in the generation of a gas stream in the column by blowing in gaseous or superheated phosgene and/or inert solvent and/or inert gases.

The mean residence time in the column is between 10 min and 12 h, preferably 15 min-11 h and more preferably 15 min-10 h.

The bottom temperature in the distillation column is generally between 90° C. and 250° C., preferably between 100° C. and 240° C. and more preferably between 110 and 230° C. The top pressure in the distillation column is generally between 1.1 bar abs and 80 bar abs, preferably between 1.5 and 50 bar abs, more preferably between 2 and 35 bar abs, even more preferably between 3 and 10 bar abs and especially between 4 and 8 bar abs.

At the bottom of the column, a liquid and/or gaseous stream comprising the isocyanate as the product is then withdrawn.

The phosgenation in the gas phase can be effected, for example, as described in EP 1 275 639 A1, EP 1 275 640 A1, EP 1 449 826 A1, DE 10359627 A1 or in German patent application DE 102005042392.

The gas phase phosgenation can preferably be performed as follows:

In the gas phase phosgenation, the aim is by definition that the compounds which occur in the course of the reaction, i.e. reactants (diamine and phosgene), intermediates (especially the mono- and dicarbamoyl chlorides formed as intermediates), end products (diisocyanate), and any inert compounds metered in, remain in the gas phase under the reaction conditions. Should these or other components separate out of the gas phase, for example at the reactor wall or other apparatus components, these deposits can undesirably change the heat transfer or the flow through of the components in question. This is especially true of amine hydrochlorides which occur, which form from free amino groups and hydrogen chloride (HCl), since the resulting amine hydrochlorides precipitate out easily and are only evaporable again with difficulty.

The reactants, or else only one of them, can be metered into the mixing chamber together with at least one inert medium.

The inert medium is a medium which is present in gaseous form in the reaction chamber at the reaction temperature and does not react with the compounds which occur in the course of the reaction. The inert medium is generally mixed with amine and/or phosgene before the reaction, but can also be metered in separately from the reactant streams. For example, nitrogen, noble gases such as helium or argon, or aromatics such as chlorobenzene, chlorotoluene, o-dichlorobenzene, toluene, xylene, chloronaphthalene, decahydronaphthalene, carbon dioxide or carbon monoxide can be used. Preference is given to using nitrogen and/or chlorobenzene as the inert medium.

In general, the inert medium is used in such an amount that the ratio of the gas volumes of inert medium relative to amine or to phosgene is from more than 0.0001 to 30, preferably from more than 0.01 to 15, more preferably from more than 0.1 to 5.

Before the process according to the invention is performed, the starting amines are evaporated and heated to from 200° C. to 600° C., preferably from 300° C. to 500° C., and fed to the reactor through the mixing unit if appropriate diluted with an inert gas or with the vapors of an inert solvent.

Before the process according to the invention is performed, the phosgene used in the phosgenation, if appropriate diluted with an inert gas or with the vapors of an inert solvent, is likewise heated to a temperature within the range from 200° C. to 600° C., preferably from 300° C. to 500° C.

According to the invention, phosgene is used in excess based on amino groups. Typically, a molar ratio of phosgene to amino groups of from 1.1:1 to 20:1, preferably from 1.2:1 to 5:1, is present.

The reaction sets in generally on contact of the reactants immediately after the mixing.

In the mixing unit, the reactant streams are mixed substantially fully within a short time.

To perform the inventive reaction, the preheated stream comprising amine or mixtures of amines and the preheated stream comprising phosgene are passed continuously into the reactor, preferably a tubular reactor.

The reactors consist generally of steel, glass, alloyed or enameled steel, and have a length which is sufficient to enable full reaction of the diamine with the phosgene under the process conditions.

It is generally possible to use the reactor designs known from the prior art. Examples of reactors are known from EP-B1 289840, column 3 line 49-column 4 line 25, EP-B1 593334, WO 2004/026813, page 3 line 24-page 6 line 10, WO 03/045900, page 3 line 34-page 6 line 15, EP-A1 1275639, column 4 line 17-column 5 line 17, and EP-B1 570799, column 2 line 1-column 3 line 42, each of which is incorporated explicitly within this disclosure.

Preference is given to using tubular reactors.

The reaction of phosgene with amine in the reaction chamber is effected at absolute pressures of from more than 0.1 bar to less than 20 bar, preferably between 0.5 bar and 15 bar and more preferably between 0.7 and 10 bar. In the case of the conversion of (cyclo)aliphatic amines, the absolute pressure is most preferably between 0.7 bar and 5 bar, in particular from 0.8 bar to 3 bar and especially from 1 to 2 bar.

In general, the pressure in the feed lines to the mixing apparatus is higher than the above-specified pressure in the reactor. This pressure declines according to the selection of the mixing apparatus. The pressure in the feed lines is preferably from 20 to 2000 mbar, more preferably from 30 to 1000 mbar, higher than in the reaction chamber.

In the process according to the invention, phosgene is reacted with amine in the gas phase. The reaction in the gas phase is understood to mean that the conversion of the reactant streams and intermediates react with one another to give the products in the gaseous state and, in the course of the reaction, during passage through the reaction chamber remain in the gas phase to an extent of at least 95%, preferably to an extent of at least 98%, more preferably to an extent of at least 99%, even more preferably to an extent of at least 99.5%, in particular to an extent of at least 99.8% and especially to an extent of at least 99.9%.

Intermediates are, for example, the monoaminomonocarbamoyl chlorides formed from the diamines, dicarbamoyl chlorides, monoamino monoisocyanates and monoisocyanatomonocarbamoyl chlorides, and the hydrochlorides of the amino compounds.

In the process according to the invention, the temperature in the reaction chamber is selected such that it is above the boiling point of the diamine used, based on the pressure conditions existing in the reaction chamber. According to the amine used and pressure established, there typically arises an advantageous temperature in the reaction chamber of more than 200° C., preferably more than 260° C. and more preferably more than 300° C. In general, the temperature is up to 600° C., preferably up to 570° C.

The mean contact time of the reaction mixture in the process according to the invention is generally between 0.001 second and less than 5 seconds, preferably from more than 0.01 second to less than 3 seconds, more preferably from more than 0.015 second to less than 2 seconds. The mean contact time even more preferably from 0.015 to 1.5 seconds, in particular from 0.015 to 0.5 second, especially from 0.020 to 0.1 second and often from 0.025 to 0.05 second is.

The gaseous reaction mixture preferably passes through the reaction chamber at a flow rate of from 10 to 300 meter/second, preferably from 25 to 250 meters/second, more preferably from 40 to 230, even more preferably from 50 to 200, in particular from more than 150 to 190 and especially from 160 to 180 meters/second.

The turbulent flow achieves narrow residence times with a low standard deviation of usually not more than 6%, as described in EP 570799, and good mixing. Measures, for example the constriction described in EP-A-593 334, which is additionally prone to blockage, are not necessary.

After the reaction, the gaseous reaction mixture is preferably washed at temperatures greater than 130° C. with a solvent (quench). Suitable solvents are preferably hydrocarbons which are optionally substituted by halogen atoms, for example hexane, benzene, nitrobenzene, anisole, chlorobenzene, chlorotoluene, o-dichlorobenzene, trichlorobenzene, diethyl isophthalate (DEIP), tetrahydrofuran (THF), dimethylformamide (DMF), xylene, chloronaphthalene, decahydronaphthalene and toluene. The solvent used is more preferably monochlorobenzene. The solvent used may also be the isocyanate. The wash transfers the isocyanate selectively into the wash solution. Subsequently, the remaining gas and the resulting wash solution are preferably separated by means of rectification into isocyanate, solvent, phosgene and hydrogen chloride.

Once the reaction mixture has been converted in the reaction chamber, it is conducted into the workup apparatus with quench. This is preferably a so-called wash tower, wherein the isocyanate formed is removed from the gaseous mixture by condensation in an inert solvent, while excess phosgene, hydrogen chloride and if appropriate the inert medium pass through the workup apparatus in gaseous form. Preference is given to keeping the temperature of the inert solvent above the dissolution temperature of the carbamoyl chloride corresponding to the amine in the selected quench medium. More preferably, the temperature of the inert solvent is kept above the melting point of the carbamoyl chloride corresponding to the amine.

In general, the pressure in the workup apparatus is lower than in the reaction chamber. The pressure is preferably from 50 to 500 mbar, more preferably from 80 to 150 mbar, lower than in the reaction chamber.

The wash can be carried out, for example, in a stirred vessel or in other conventional apparatus, for example in a column or mixer-settler apparatus.

In terms of process technology, for a wash in the process according to the invention, it is possible to use all extraction and washing processes and apparatus known per se, for example those which are described in Ullmann's Encyclopedia Industrial Chemistry, 6th ed, 1999 Electronic Release, chapter: Liquid—Liquid Extraction Apparatus. For example, these may be single-stage or multistage, preferably single-stage, extractions, and those in cocurrent or countercurrent mode, preferably countercurrent mode.

A suitable quench is, for example, known from EP-A1 1403248, column 2 line 39-column 3 line 18, which is explicitly incorporated within this disclosure.

In this quench zone, the reaction mixture, which consists essentially of the isocyanates, phosgene and hydrogen chloride, is mixed intensively with the liquid sprayed in. The mixing is effected in such a way that the temperature of the reaction mixture is lowered proceeding from 200 to 570° C. to from 100 to 200° C., preferably to from 140 to 180° C., and the isocyanate present in the reaction mixture is transferred by condensation fully or partly into the liquid droplets sprayed in, while the phosgene and the hydrogen chloride remain essentially completely in the gas phase.

The proportion of the isocyanate which is present in the gaseous reaction mixture and is transferred to the liquid phase in the quench zone is preferably from 20 to 100% by weight, more preferably from 50 to 99.5% by weight and especially from 70 to 99% by weight, based on the isocyanate present in the reaction mixture.

The reaction mixture flows through the quench zone preferably from the top downward. Below the quench zone is arranged a collecting vessel in which the liquid phase is separated out, collected and removed from the reaction chamber via an outlet, and subsequently worked up. The remaining gas phase is removed from the reaction chamber via a second outlet and likewise worked up.

The quench can, for example, be effected as described in EP 1403248 A1, or as described in international application WO 2005/123665.

To this end, the liquid droplets are obtained by means of one- or two-substance atomizer nozzles, preferably one-substance atomizer nozzles, and, according to the embodiment, generate a spray cone angle of from 10 to 140°, preferably from 10 to 120°, more preferably from 10° to 100°.

The liquid which is sprayed in via the atomizer nozzles must have a good solubility for isocyanates. Preference is given to using organic solvents. In particular, aromatic solvents which are substituted by halogen atoms are used.

The workup of the diisocyanate thus obtained can be effected in a manner known per se, for example as described above for the liquid phase phosgenation.

The present invention further provides 1,5-pentamethylene diisocyanate with a $^{14}C:^{12}C$ isotope ratio of from $0.5 \times 10^{-12}$ to $5 \times 10^{-12}$, preferably from $1.0 \times 10^{-12}$ to $4 \times 10^{-12}$ and more preferably from $1.5 \times 10^{-12}$ to $3 \times 10^{-12}$. Such 1,5-pentamethylene diisocyanate is obtainable when step a) or b) is performed proceeding from biological material.

The advantage of such 1,5-pentamethylene diisocyanate is that it has a $^{14}C$ isotope content which corresponds to natural material, whereas 1,5-pentamethylene diisocyanate which is prepared on a petrochemical basis has an unnatural content, which is generally below $0.3 \times 10^{-12}$, usually below $0.2 \times 10^{-12}$ and usually below $0.1 \times 10^{-12}$. Owing to its isotope content, this inventive 1,5-pentamethylene diisocyanate can then be used to synthesize compounds for use as probes for, for example, $^{14}C$ studies.

The present invention further provides 1,5-pentamethylene diisocyanate which additionally has a total chlorine content below 50 ppm by weight and a content of hydrolyzable chlorine below 10 ppm by weight. Such 1,5-pentamethylene diisocyanate is obtainable when step c) is performed without phosgene. In this way, it is possible to obtain 1,5-pentamethylene diisocyanate which has been prepared entirely without petrochemistry and chlorine chemistry.

The 1,5-pentamethylene diisocyanate prepared in accordance with the invention is suitable, as a result of its advantageous properties detailed above, advantageously for preparing polyisocyanates having isocyanurate groups, polyisocyanates having uretdione groups, polyisocyanates having biuret groups, polyisocyanates having urethane or allophanate groups, polyisocyanates comprising oxadiazinetrione groups or iminooxadiazinedione groups, and/or uretonimine-modified polyisocyanates.

Such polyisocyanates find use, for example, in the production of plastics comprising urethane, isocyanurate, amide and/or urea groups by the polyisocyanate polyaddition process. Such polyisocyanate mixtures are used especially to produce light-stable polyurethane lacquers and coatings.

The polyisocyanates thus obtainable, which are based on the 1,5-pentamethylene diisocyanate prepared in accordance with the invention, are generally used in the paints industry. The inventive mixtures can be used, for example, in coating compositions for 1K or 2K polyurethane coatings, for example for primers, surfacers, basecoats, unpigmented topcoats, pigmented topcoats and clearcoats in the sector of industrial coating, especially aircraft coating or large vehicle coating, wood coating, automotive finishing, especially OEM finishing or refinishing, or decorative coating. The coating compositions are particularly suitable for applications in which a particularly high application safety, external weathering stability, appearance, solvent stability and/or chemical stability are required. The curing of these coating compositions is insignificant in the context of the invention. Especially in the automotive industry, multicoat cures, for example of clearcoat and basecoat (so-called two-in one), or of surfacer, clearcoat and basecoat (so-called three-in-one), are increasingly being carried out.

In addition, the 1,5-pentamethylene diisocyanate prepared in accordance with the invention can be used to prepare thermoplastic polyurethanes (TPUs), as described, for example, in Kunststoffhandbuch [Plastics Handbook], volume 7 "Polyurethane", Carl Hanser Verlag Munich, Vienna, $3^{rd}$ edition 1993, pages 455 to 466.

They are prepared by reacting diisocyanates with compounds having at least two hydrogen atoms reactive with isocyanate groups, preferably difunctional alcohols.

The isocyanate-reactive compounds used may be commonly known polyhydroxyl compounds having molecular weights of from 500 to 8000, preferably from 600 to 6000, especially from 800 to 4000, and preferably of a mean functionality of from 1.8 to 2.6, preferably from 1.9 to 2.2, especially 2, for example polyesterols, polyetherols and/or polycarbonatediols. Preference is given to using polyesterdiols which are obtainable by reacting butanediol and hexanediol as the diol with adipic acid as the dicarboxylic acid, where the weight ratio of butanediol to hexanediol is preferably 2 to 1. Preference is further given to polytetrahydrofuran having a molecular weight of from 750 to 2500 g/mol, preferably from 750 to 1200 g/mol.

The chain extenders used may be commonly known compounds, for example diamines and/or alkanediols having from 2 to 10 carbon atoms in the alkylene radical, especially ethylene glycol and/or butanediol-1,4, and/or hexanediol and/or di- and/or trioxyalkylene glycols having from 3 to 8 carbon atoms in the oxyalkylene radical, preferably corresponding oligo(polyoxypropylene glycols), and it is also possible to use mixtures of the chain extenders. The chain extenders used may also be 1,4-bis(hydroxymethyl)benzene (1,4-BHMB), 1,4-bis(hydroxyethyl)benzene (1,4-BHEB) or 1,4-bis(2-hydroxyethoxy)benzene (1,4-HQEE). Preferred chain extenders are ethylene glycol and hexanediol, more preferably ethylene glycol.

Typically, catalysts which accelerate the reaction between the NCO groups of the diisocyanates and the hydroxyl groups of the formation components are used, for example tertiary amines such as triethylamine, dimethylcyclohexylamine, N-methyl-morpholine, N,N'-dimethylpiperazine, 2-(dimethylaminoethoxy)ethanol, diazabicyclo[2.2.2]octane and the like, and also especially organic metal compounds such as titanic esters, iron compounds, for example iron(III) acetylacetonate, tin compounds such as tin diacetate, tin dilaurate, or the dialkyltin salts of aliphatic carboxylic acids such as dibutyltin diacetate, dibutyltin dilaurate or the like. The catalysts are used typically in amounts of from 0.0001 to 0.1 part by weight per 100 parts by weight of polyhydroxyl compound.

As well as catalysts, customary assistants can also be added to the formation components to. Examples include surface-active substances, flame retardants, nucleators, lubricating and demolding aids, dyes and pigments, inhibitors, stabilizers against hydrolysis, light, heat, oxidation or discoloration, stabilizers against microbial degradation, inorganic and/or organic fillers, reinforcers and plasticizers.

The TPUs are prepared usually by customary processes, such as by means of belt systems or reaction extruders.

To prepare expanded TPU, the TPUs are preferably mixed with expandable microspheres and processed thermoplastically to the desired shaped bodies. This can be done, for example, by means of injection molding, sintering or by means of extrusion. The temperature in the thermoplastic processing results in an expansion of the expandable microspheres and hence in the formation of the expanded TPU. The melt is preferably introduced into the molds and cures there.

Expanded TPUs can be used, for example, as films, pipes, profiles, fibers, cable, shoe soles, other shoe parts, earmarks, automobile parts, agricultural products, electrical products, damping elements; arm rests; plastic furniture elements, ski boots, stop buffers, rollers, ski goggles, powder slush surfaces.

It is an advantage of the process according to the invention that it permits, for the first time, industrial scale preparation of 1,5-pentane diisocyanate. The term "industrial scale" in this document is understood to mean the production of at least 50 tonnes/year, preferably at least 500 tonnes/year and more preferably at least 1000 tonnes/year.

The invention claimed is:

1. A process for preparing pentamethylene 1,5-diisocyanate, which comprises:
   a) preparing lysine from a suitable substrate;
   b) converting lysine to 1,5-pentanediamine and
   c) converting the 1,5-pentanediamine thus obtained to pentamethylene 1,5-diisocyanate
   wherein said pentamethylene 1,5-diisocyanate has a $^{14}$C:$^{12}$C isotope ratio of from $0.5 \times 10^{-12}$ to $5 \times 10^{-12}$.

2. Pentamethylene 1,5-diisocyanate prepared by a process according to claim 1.

3. The process according to claim 1, wherein step b) is performed in the presence of an enzyme.

4. The process according to claim 1, wherein lysine is decarboxylated thermally in the absence of a catalyst in step b).

5. The process according to claim 1, wherein step b) is performed in the presence of a catalyst which is different than an enzyme.

6. The process according to claim 1, wherein the suitable substrate is selected from the group consisting of wood, cellulose, starch, monomeric carbohydrates, chitin, animal fats, vegetable fats, animal oils, vegetable oils, proteins, virgin wool, leather, skins, tallow, gelatin, casein and straw.

7. The process according to claim 1, wherein the suitable substrate comprises monosaccharides, oligosaccharides, polysaccharides, oils, fats, fatty acids, alcohols or organic acids.

8. The process according to claim 1, wherein the suitable substrate is glucose, sucrose, lactose, fructose, maltose, molasses, starch or cellulose.

9. The process according to claim 1, wherein lysine or a lysine base structure is formed intracellularly.

10. The process according to claim 1, wherein step c) is performed without phosgene.

11. The process according to claim 1, wherein step c) is performed in the presence of liquid phosgene.

12. The process according to claim 1, wherein step c) is performed in the presence of gaseous phosgene.

13. Polyisocyanates or thermoplastic polyurethanes prepared from the pentamethylene 1,5-diisocyanate according to claim 2.

* * * * *